United States Patent [19]
Shiroyama et al.

[11] Patent Number: 5,850,837
[45] Date of Patent: Dec. 22, 1998

[54] DEVICE FOR CORRECTING AN INGROWN NAIL

[75] Inventors: Kaisuke Shiroyama, Zama; Tatsuhiko Ueki, Yokohama; George Murota, Tokyo, all of Japan

[73] Assignees: Furukawa Electric Co., Ltd., Tokyo; Furukawa Techno Material Co., Ltd., Hiratsuka, both of Japan

[21] Appl. No.: 819,911

[22] Filed: Mar. 18, 1997

[30] Foreign Application Priority Data

Mar. 21, 1996 [JP] Japan .................................... 8-064747
Mar. 21, 1996 [JP] Japan .................................... 8-064748

[51] Int. Cl.⁶ .................................................... A61F 13/06
[52] U.S. Cl. ........................................... 128/892; 128/893
[58] Field of Search .................................... 128/845, 846, 128/892, 893

[56] References Cited

U.S. PATENT DOCUMENTS 2,505,086  4/1950  Andrews .
4,057,055  11/1977  Clark .
4,674,486  6/1987  Hoffman .
5,626,612  5/1997  Bartlett ................................. 606/232

FOREIGN PATENT DOCUMENTS 8-215227  8/1996  Japan .

Primary Examiner—Michael A. Brown
Attorney, Agent, or Firm—Frishauf, Holtz, Goodman, Langer & Chick

[57] ABSTRACT

A device which is installed onto an ingrown nail of a human toe to correct the ingrown nail, includes a support member affixed to the ingrown nail, and a correcting member supported by the support member and effecting force on the ingrown nail toward the correcting direction for the ingrown portion of the nail. The correcting member may be formed of a superelastic material which is shape-memory-treated to memorize a first shape, and which is deformed to a second shape different from the first shape so as to be installed onto a surface of the ingrown nail of the human toe in the second shape.

4 Claims, 13 Drawing Sheets

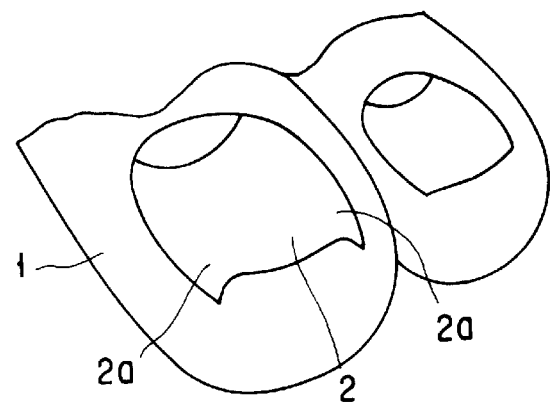
F I G. 1
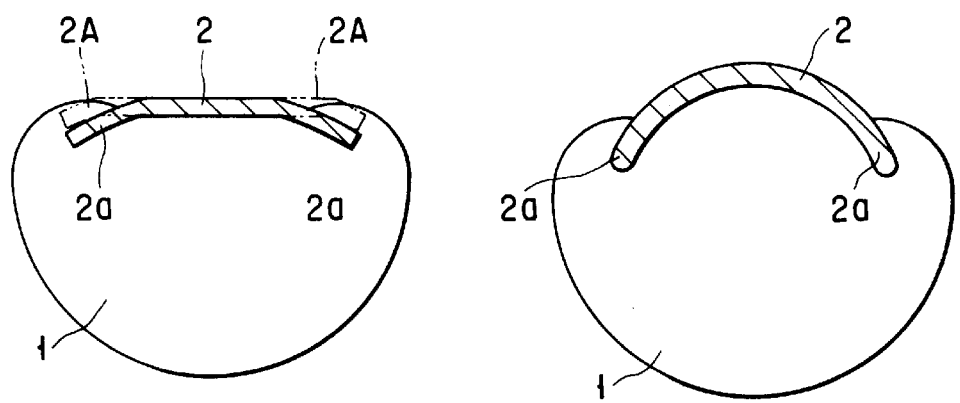
F I G. 2A    F I G. 2B
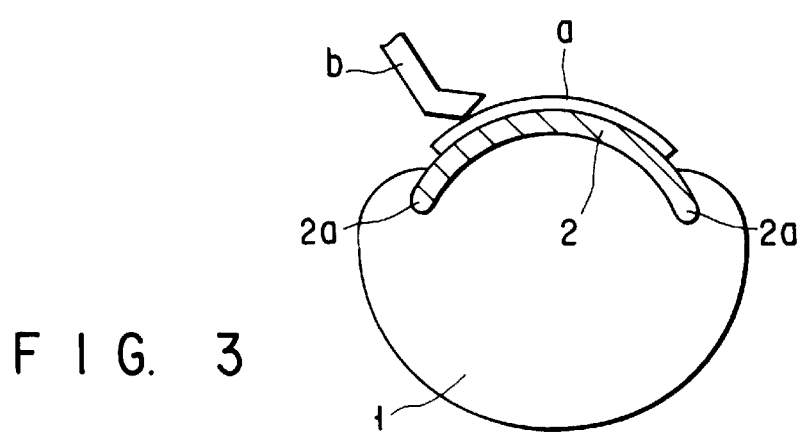
F I G. 3

DEFORMATION OF ORDINARY METAL

SHAPE MEMORY EFFECT

SUPERELASTIC EFFECT

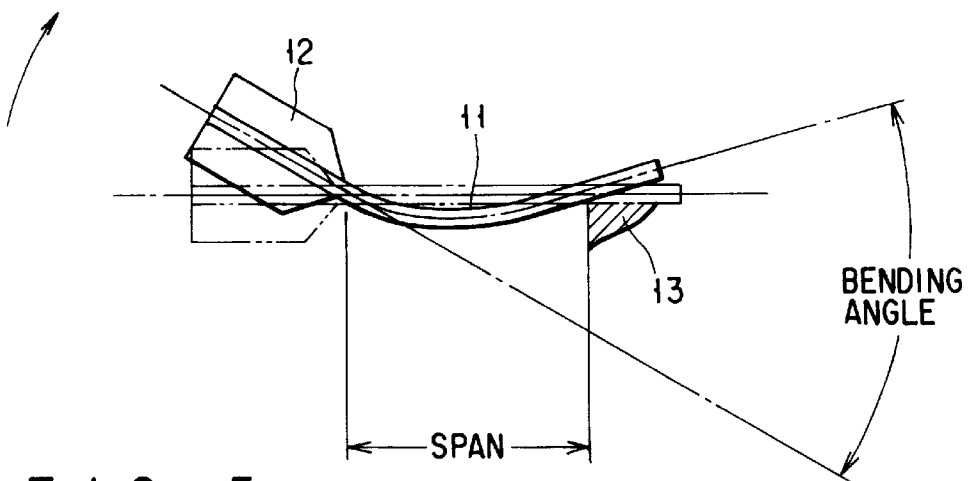
F I G. 5
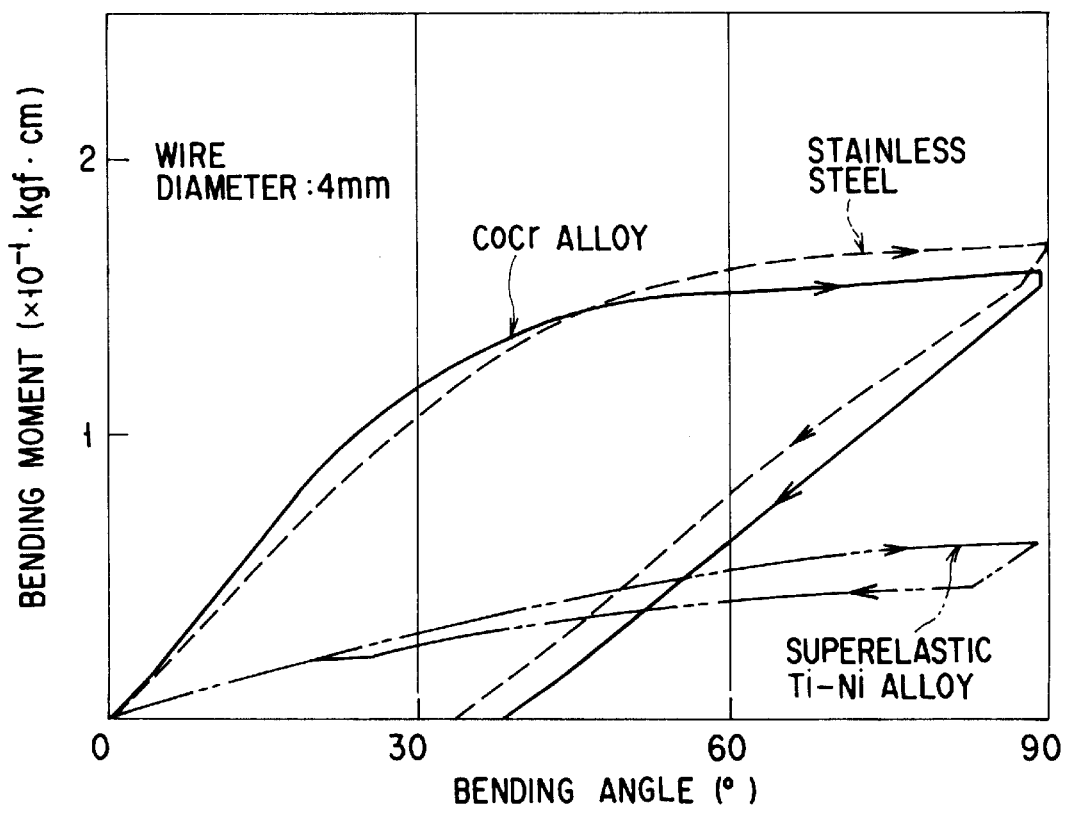
F I G. 6

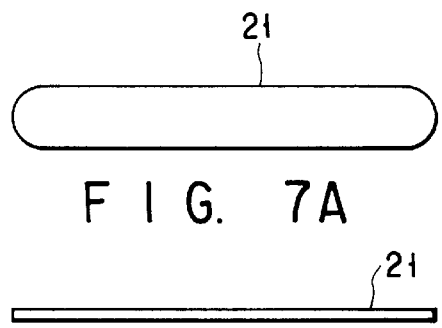
F I G. 7A
F I G. 7B
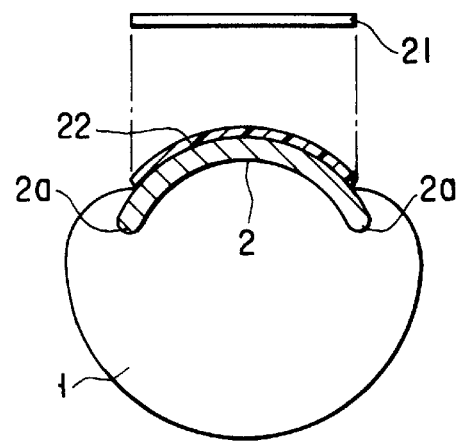
F I G. 8
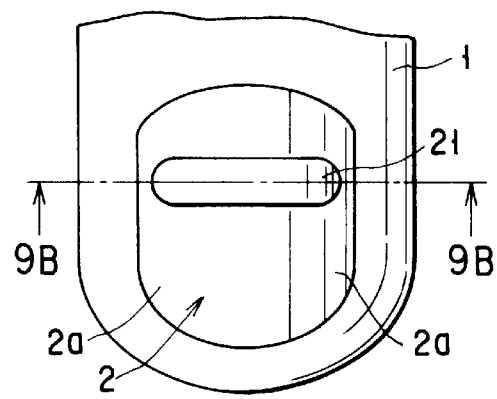
F I G. 9A
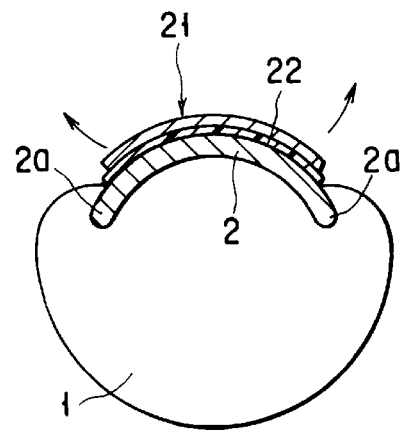
F I G. 9B
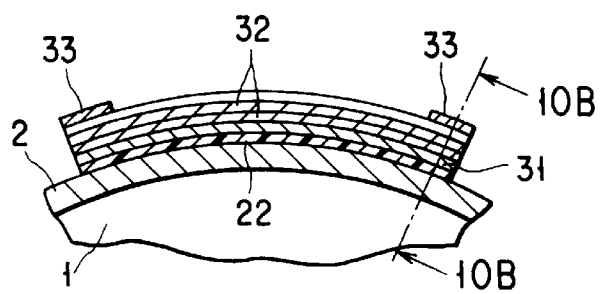
F I G. 10A
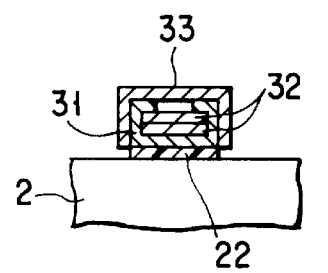
F I G. 10B

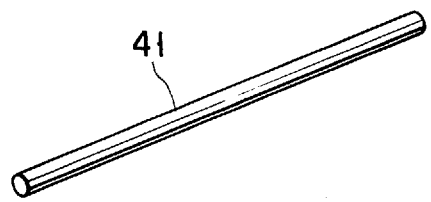
F I G. 11A
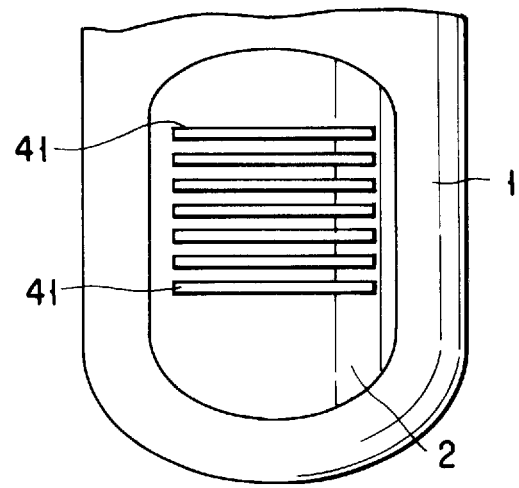
F I G. 11B
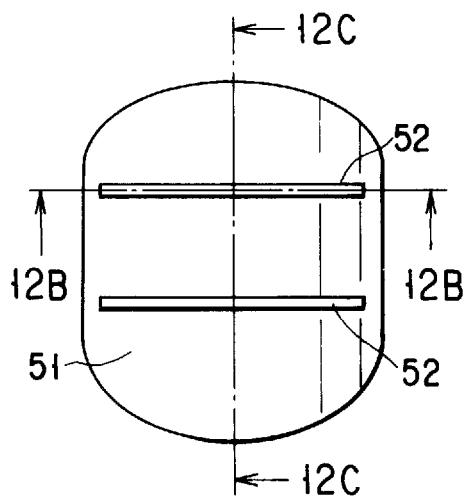
F I G. 12A
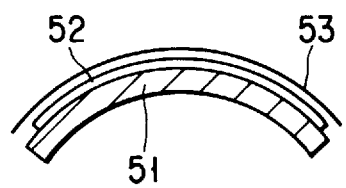
F I G. 12B
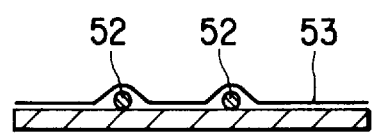
F I G. 12C

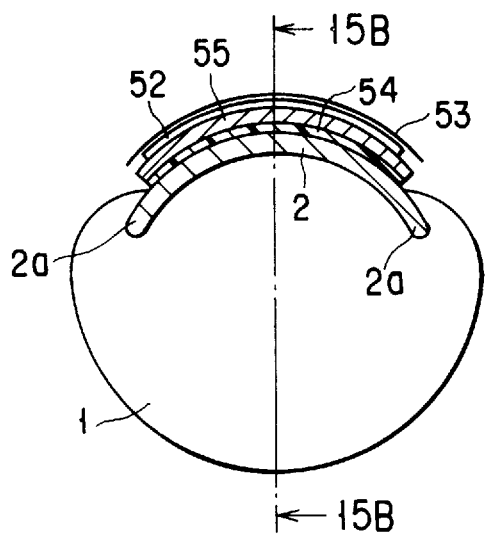
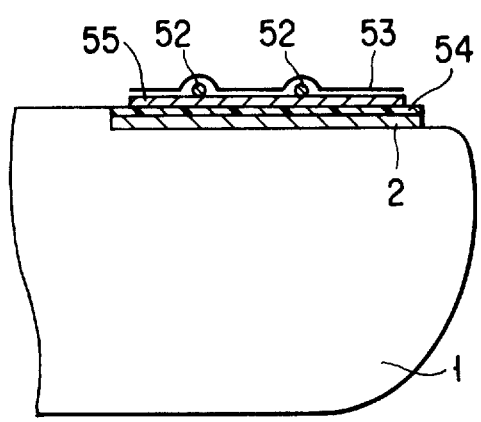
F I G. 15A  F I G. 15B
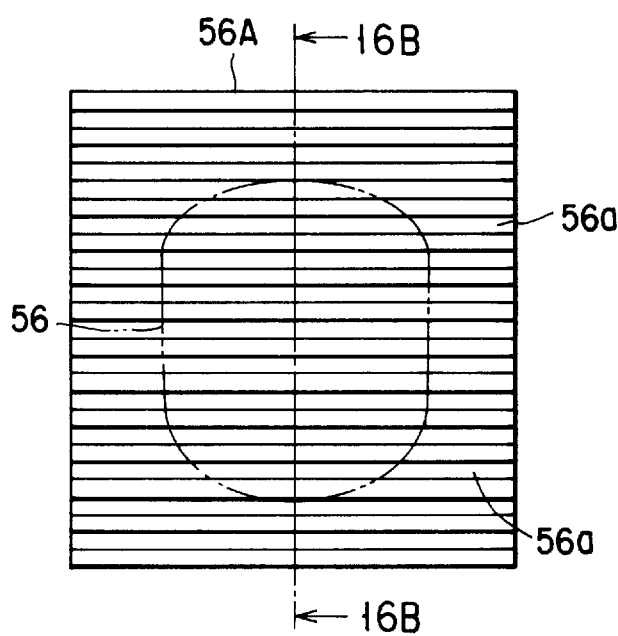
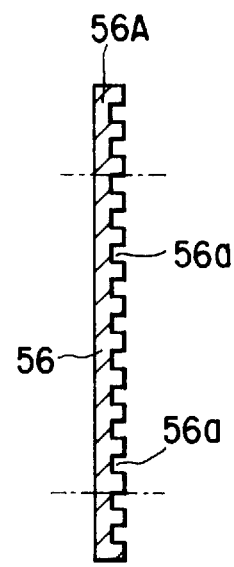
F I G. 16A  F I G. 16B

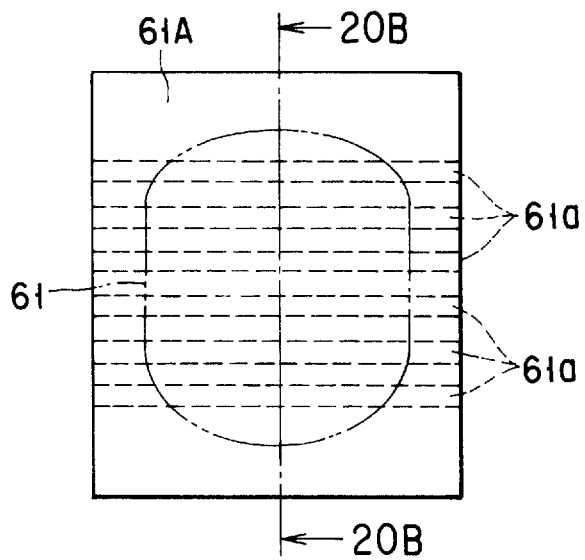
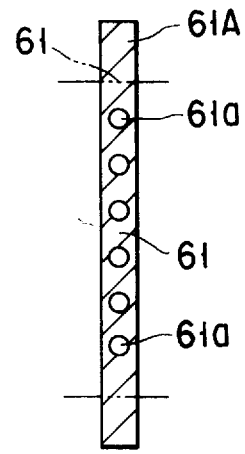
F I G. 20A    F I G. 20B
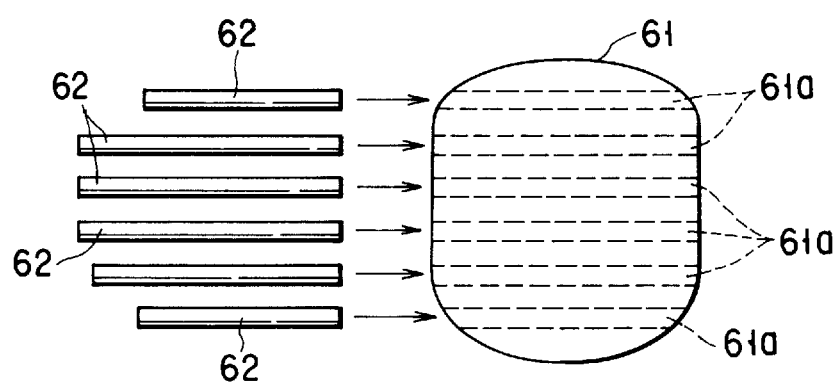
F I G. 21

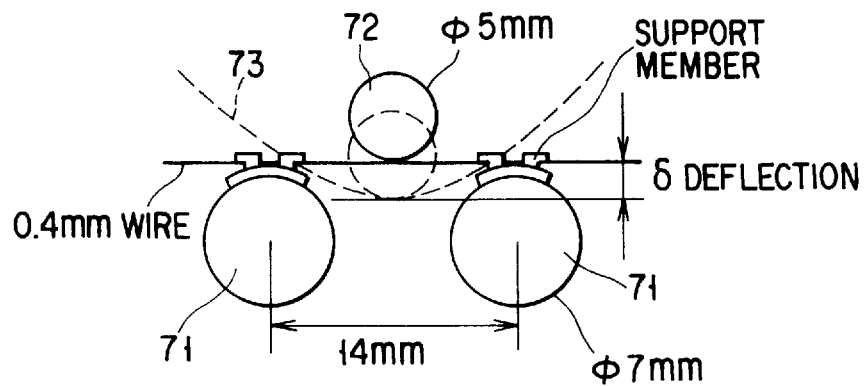
F I G. 25
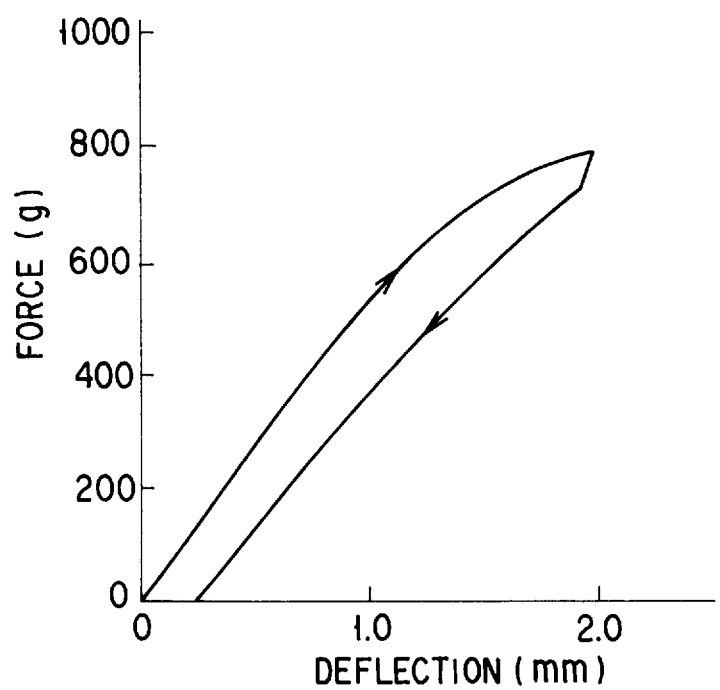
F I G. 26

DEVICE FOR CORRECTING AN INGROWN NAIL

BACKGROUND OF THE INVENTION

This invention relates to a device for correcting an ingrown nail and a method for installing the device onto a toenail.

As shown in FIGS. 1, 2A, and 2B, an ingrown nail is a disease, in which the shape of side edges (ingrown portion 2a) of a nail 2 of a toe 1 are deformed into an involute-like curvature and become embedded in the tissue of the toe 1, thereby pressing the tissue to cause incidence of pain.

FIG. 2A shows the side edges of the nail 2 bending more inwardly compared with a normal nail 2A traced with the dotted line and which become embedded in the tissue. FIG. 2B shows a more serious ingrown nail, in which a degree of curvature is further increased. Such an ingrown nail causes incidence of intense pain when a person puts on shoes and presses the toe 1 downward.

As a method for treating the ingrown nail other than surgical removal, there is a method using a corrective device (a) made of a plate-like member of a size similar to the width of nail 2, the plate-like member being entirely composed of a spring material made from special steel or a synthetic resin as shown in FIG. 3. An adhesive is applied on the back surface of the corrective device (a). The corrective device (a) is then placed in the middle of the surface of the nail 2 and is then pressed with bar (b) so that the device (a) is affixed to the surface of the nail 2.

At this time, the corrective device (a) is forcibly curved in compliance with the shape of the surface of the nail 2 to be affixed to the nail 2. For this, the corrective device generates an elastically restoring force so as to be restored to the original shape. The elastically restoring force acts on the nail 2 to correct the nail 2 so that the ingrown portion of the nail 2 is normally corrected.

As shown by the above illustration, conventionally, there have been methods developed to correct the ingrown nail using corrective devices formed from metals such as a special steel, or resins. In this method, the corrective devices act on the nail utilizing restoring force to keep the original shape in the range limited to the elasticity of the material to be used.

Special steel possesses large restoring force due to a high elastic modulus so that a thin corrective device can be made using the special steel. However, the elastic strain of the device made of the special steel is 0.5% at the most. When the device is deformed with force so far required for a 0.1 mm thickness tape to be wrapped around a thin rod with a radius of curvature of less than 10 mm, the deformation of the device remains. Excess force for bending the device to be applied on the nail causes permanent deformation, exhibiting a problem that the restoring force of the special steel can not be utilized. Also, corrective devices made of metals tends to lose restoring force in the course of restoration to the original shape, thereby requiring an exchange of the devices.

When synthetic resins are used as a material for the corrective device, sufficient force acting on the nail can not be produced. Therefore, it is considered to make the thick corrective device because the synthetic resin has a lower elastic modulus. However, if a thick corrective device is used, it can be bonded to portions largely bent of the nail only with difficulties and easily peeled off, thereby presenting a problem of difficulties in actual use.

Additionally, conventionally corrective devices require complicated processes when directly installing the elastic material onto the nail. Specifically, it is required for the corrective device to be pressed on the nail until the corrective device is bonded to the nail and to be bent in compliance with the curvature of the nail when bonding the corrective device to the nail.

Also, because the conventional corrective devices are entirely made from metals or resins, they can only utilize the elastic force of the metals or resins which is allowed to directly act on the nail as the corrective force. Specifically, the conventional corrective devices are intended to correct the ingrown nail by applying a large elastic force per unit area to the nail so as to correct the ingrown portion of the nail. The large force per unit area given by the conventional corrective devices allows the nail to be bent toward the correcting direction. As a result, the ingrown portion of the nail is forced to receive a heavy load, which sometimes causes incidence of pain at the ingrown portion of the nail.

BRIEF SUMMARY OF THE INVENTION

An object of the present invention is to provide a device for correcting ingrown nail which can be made thin, continuously act on the nail utilizing a stable corrective force, thereby exhibiting excellent corrective characteristics, and is remarkably reliable.

Another object of the present invention is to provide a device capable of correcting an ingrown portion of the nail without a large forcible load given on the ingrown portion of the nail and also being readily installed onto to the nail.

A further object of the present invention is to provide a method for installing the device for correcting the ingrown nail onto the nail.

According to the present invention, a correcting device which is adapted to be installed onto an ingrown nail of a human toe to correct the ingrown nail, comprises a superelastic tape or a superelastic wire consisting essentially of nickel/titanium alloy which is shaped-memory-treated to memorize a first shape, and which is deformed to a second shape different from the first shape so as to be installed onto a surface of the nail of the human toe in the second shape.

According to another aspect of the present invention, a device for correcting an ingrown nail, which is adapted to be installed onto a nail of a human toe, comprises a support member to be installed onto the nail; and a correcting member supported by the support member and effecting force on the nail in a correcting direction of the nail. The support member has a larger area than that of the correcting member. The correcting member is formed of one of a superelastic tape and a superelastic wire and consists essentially of nickel/titanium alloy which is placed and fixed onto, or which is embedded in, the support member.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a perspective view of an ingrown toenail;

FIGS. 2A and 2B are respectively an end view of an ingrown toenail;

FIG. 3 is a schematic view of a conventional device for correcting an ingrown nail;

FIG. 5 is a diagram for illustrating a test method for bending ordinary metals and superelastic alloys.

FIG. 6 is a graph showing the results of the bending test corresponding to the FIG. 5.

FIGS. 7A and 7B are respectively a top plan view and a front elevation of a first embodiment of the device for correcting an ingrown nail;

FIG. 8 is a view showing a relation between the device for correcting an ingrown nail and the toenail corresponding to the FIGS. 7A and 7B;

FIGS. 9A and 9B are a top plan view and a sectional view along the line 9B respectively showing a configuration wherein the device for correcting an ingrown nail is placed on the toenail corresponding to the FIGS. 7A and 7B;

FIGS. 10A and 10B are views showing an alternative embodiment of the device for correcting an ingrown nail corresponding to the first embodiment.

FIGS. 11A and 11B are views showing an alternative embodiment of the device for correcting an ingrown nail corresponding to the first embodiment;

FIGS. 12A to 12C are views showing a second embodiment of a device for correcting an ingrown nail;

FIGS. 15A and 15B are views of an alternative embodiment of a device for correcting an ingrown nail corresponding to the second embodiment;

FIGS. 16A and 16B are views of an alternative embodiment of a device for correcting an ingrown nail corresponding to the second embodiment;

FIGS. 20A and 20B are views of the material for the device for correcting an ingrown nail corresponding to the second embodiment;

FIG. 21 is a view of an alternative embodiment of a device for correcting an ingrown nail corresponding to the second embodiment;

FIG. 25 is a view for explaining a method for a bending test;

FIG. 26 is a graph showing the relation between load and displacement with respect to wire of stainless steel;

DETAILED DESCRIPTION OF THE INVENTION

The device for correcting an ingrown nail corresponding to a first embodiment of the present invention is for correcting an ingrown nail and has the following characteristics. The device for correcting the ingrown nail of the present invention is formed of a superelastic material which is shape-memory-treated to memorize a specific shape. The shape of the material is deformed into a shape different from the memory shape to be installed onto the surface of the toe nail.

The superelastic effect is defined as an effect by which a material deformed by applying external force can recover the original shape when the external force is removed.

Figure 4A:
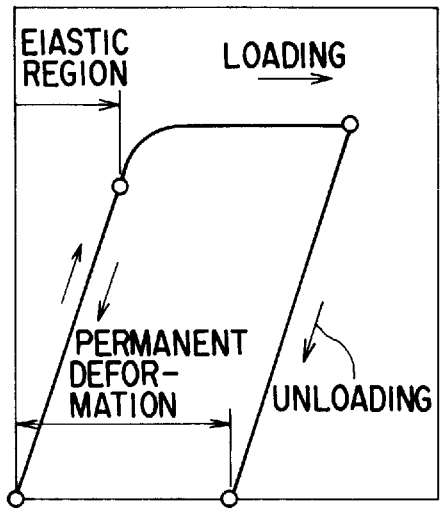
FIGS. 4A to 4C are series of graphs showing the relation of external force to elongation with respect to metals.

With respect to ordinary metals, as shown in FIG. 4A, the relation between external force and elongation is characterized in that permanent deformation remains when the external force applied on the metal is removed after applying the external force on the metal.

On the other hand, the relation of external force versus elongation for shape memory metals is characterized in the following relation. The shape memory metal is shape-memory-treated so as to restore to the original shape at over, for example, normal temperature prior to actual use. When the metal is deformed by receiving external force at a temperature (normal temperature) lower than the transformation temperature of the metal and then the external force is removed and the metal is heated, the metal can restore to the original shape. The shape of irreversible shape memory metals are incapable of being restored to the deformed shape when again processed even at normal temperature (lower temperature) after restored to the original shape.

Figure 4B:
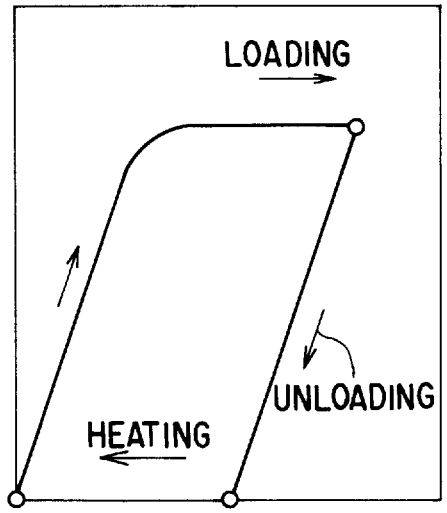
Figure 4C:
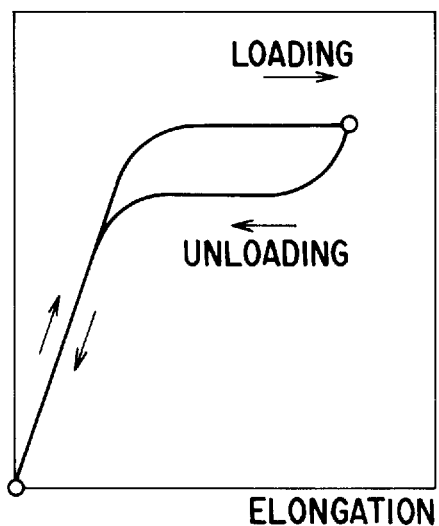
Figure 13A:
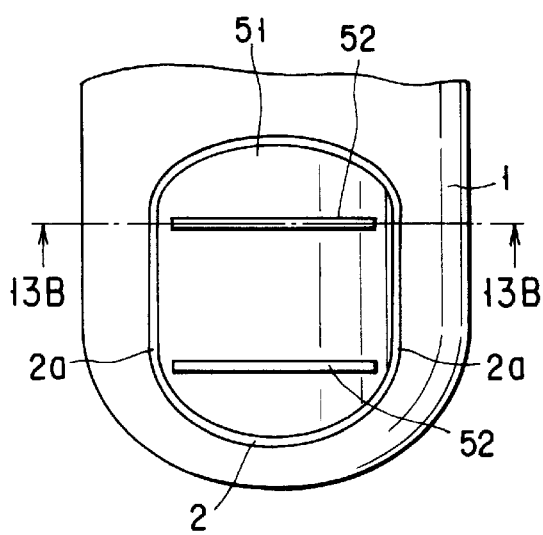
FIGS. 13A and 13B are views showing a second embodiment of a device for correcting an ingrown nail.
Figure 13B:
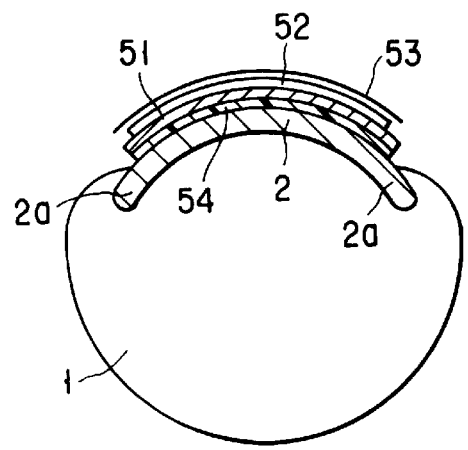

On the other hand, as shown in FIG. 4C, the relation of force versus elongation for a superelastic metal is characterized in that when the metal is shape-memory-treated to memorize a specific shape at a temperature lower than normal temperature, is deformed by receiving external force at a temperature higher than the normal temperature, and then the external force is removed, the shape of the metal is restored to the original shape at the normal temperature. Therefore, even if the superelastic metals are deformed in a deformation rate of 10% at a temperature, for example, normal temperature, higher than the transformation temperature, the shape of the metal can be restored to the memory shape by removing the external force.

As the superelastic materials, several metals are exemplified. Given as examples of the superelastic metals are copper/zinc (Cu/Zn) ternary alloys, monocrystals or polycrystals of, for example, copper/aluminum/nickel (Cu/Al/Ni) alloys, and nickel/titanium alloys. Among the Ni/Ti alloys, binary alloys including nickel in an amount of 50.5 to 52.0 at % and alloys including one or more compounds selected from the group consisting of iron (Fe), chromium (Cr), cobalt (Co), vanadium (V), copper (Cu), and the like in a total amount of less than 10 at % are desirable. Using these alloys, sufficient superelasticity can be exhibited.

The superelasticity of superelastic alloys were investigated using the following method. A filamentary test specimen formed from a Ni/Ti alloy having the superelastic effect, filamentary test specimen formed from Co/Cr alloy, and filamentary specimen with a diameter of 0.4 mm formed from stainless steel were respectively subjected to a bending test based on the ADA standard as shown in FIG. 4. In this bending test, the bending moment of the specimen was measured when the specimen was bent at an angle of 90 degrees by applying external force and the condition of strain was investigated when removing the external force after the specimen was bent at an angle of 90 degrees.

Specifically, this bending test, as shown in FIG. 5, was processed by fixing one end of a specimen 11 using a fixing member 12 and the other end of the specimen was held by a stopper 13 located with a specific span from the specimen 11. External force was applied on the specimen to bend the specimen 11. The diameter of the specimen was, for example, 0.4 mm and the span between the fixing member 12 and the stopper 13 was 25.4 mm.

The test results are shown by the graph shown in FIG. 6. From this graph, the following results are confirmed. With respect to the test specimen made from Ni/Ti alloy, when the external force was removed (unloading time) after bending the specimen at an angle of 90 degrees by applying the external force, deformation did not remain and the original shape provided before the processes was recovered.

On the other hand, with the test specimens respectively made from the stainless steel and the Co/Cr alloy, when the external force was removed (unloading time) after bending the specimen at an angle of 90 degrees by applying the external force, bending deformation of more than 30 degrees remained.

Accordingly, it is confirmed that the shape of the test specimen made from the Ni/Ti alloy having the superelastic effect can be restored to the original shape without permanent deformation after greatly bent if the external force is removed. Also, from a curve showing the relation between the bending angle and bending moment at time when the external force is removed (Unloading time), it is confirmed that an almost constant bending moment was produced.

The restoring force of the specimen made from the Ni/Ti alloy, which is produced when restoring the original shape, is smaller than those of the specimens respectively made from the stainless steel and the Co/Cr alloy, which are produced when these specimens return to their original state. However, this is because the elastic modulus of the Ni/Ti alloy is estimated to be from 6,000 to 7,000 kg/cm$^2$, and the ratio of the elastic modulus of the Ni/Ti alloy to that of the stailess steel is almost 1/3.

However, this problem can be solved by slightly alternating the shape of the device for correcting an ingrown nail, when manufacturing the device using the Ni/Ti alloy, thereby to increase the acting force of the device.

Specifically, superelastic metals can be deformed by an external force over wide range at a temperature higher than the transformation temperature. Also, in the course of restoration to the memory shape after removing the external force, change in force are small and the restoring force acts gradually and continuously on the subject.

In order to manufacture the device for correcting an ingrown nail using a superelastic alloy, the superelastic alloy is primarily shape-memory-treated to memorize a specific shape, for example, flat shape (straight line or plane) or a shape conforming with the curvature extending in the width direction of the nail. This memory-process may be carried out using known heat treatment.

When using the device for correcting an ingrown nail, the shape of the device is deformed to a shape different from the memory shape. Specifically, the device is deformed to have a shape like a circular arc conforming with entire curvature of the nail. The deformed device effects, on the nail, elastic force (restoring force) so that the shape of the device is restored to the original shape. This elastic force acts on the ingrown portion of the nail as force (corrective force), which flatters the curvature of the ingrown portion and corrects the ingrown portion to the curvature of a normal nail.

Accordingly, the device for correcting an ingrown nail, which has the superelastic effect, effects sufficiently stable restoring force on the nail gradually and continuously, thereby certainly correcting the ingrown portion of the ingrown nail without difficulties.

Also, because the device for correcting an ingrown nail effects sufficient corrective force on the nail, it is not necessary that the device is made thick in order to produce large corrective force. In addition, it is possible to solve a problem that the device cannot be installed onto the nail because of large thickness.

Accordingly, the device for correcting an ingrown nail, which is formed from superelastic materials, can effect continuously stable corrective force on the nail by the combination of elastic-deformation in a wide range due to the superelasticity and the restoring force due to appropriate elastic modulus. Therefore, the device for correcting an ingrown nail is reliable, stably exhibiting excellent corrective characteristics.

Also, the Ni/Ti alloy is used as the superelastic material to manufacture the device for correcting an ingrown nail corresponding to the first embodiment of the present invention. Therefore, the devices for correcting an ingrown nail, which sufficiently exhibit the superelasticity, can be manufactured.

Further, as the superelastic material, which is used for forming the device for correcting an ingrown nail, materials with various forms, for example, one or more cylindrical or rectangular filaments or a tape, can be used to manufacture devices for correcting an ingrown nail, which sufficiently exhibit the superelasticity.

Next, the device for correcting an ingrown nail corresponding to the first embodiment will be illustrated in more detail.

FIGS. 7A and 7B are respectively a top plan view and a front elevation of a first embodiment of a device 21 for correcting an ingrown nail (hereinafter simply called correcting device). FIG. 8 is a view showing a configuration in which the correcting device 21 is installed onto a human hallux. In FIG. 8, reference numerals 1 and 2 respectively denote a human hallux and a nail of the hallux 1. At the side edge of the nail 2, an ingrown portion 2a is formed.

The correcting device 21 is formed of a tape. If the correcting device 21 is, as shown in FIG. 8, installed onto the nail 2 of the hallux 1 along the direction of growth of the nail 2 in consideration of the lateral size of the nail 2 of the hallux 1 to be corrected, the correcting device must be sized so as to be installed onto the ingrown portion 2a. The correcting device 21 is composed of a tape of, for example, a width of 3 mm, a length of 14 mm, and a thickness of 0.2 mm.

This correcting device 21 is made from a superelastic material, for example, a plate of a Ni/Ti alloy. Among the Ni/Ti alloys, binary alloys including nickel in an amount of more than 50.5 at % and alloys including one or more metals of iron (Fe), chromium (Cr), cobalt (Co), vanadium (V), copper (Cu), and the like in a total amount of not more than 10 at % can be used.

The correcting device 21 is manufactured by shape-memory-treated for itself to have a memory of a flat shape, with setting up as a transformation temperature (Af), for example, 27° C. which is not more than 30° C. which is lower than temperature of human body.

When the correcting device 21 is installed onto the nail 2 of the hallux 1, as shown in FIG. 8, an appropriate adhesive agent is applied on the surface of the nail 2 and the device 21 is placed on the adhesive agent 22 in the width direction of the nail 2. As the adhesive agent 22, those having no adverse influence on the nail 2 and human body are selected.

The nail 2 usually curves in the width direction of the nail 2. Therefore, the device 21 is bent so that the correcting device 21 curves in the width direction of the nail 2 and fixed to the surface of the nail 2 via the adhesive agent 23. The correcting device 21 is also fixed to the ingrown portion 2a produced at both the side edges.

Then, external force is applied on the correcting device 21 until the device 21 is certainly fixed to the surface of the nail 2. By this, as shown in FIGS. 9A and 9B, the shape of the correcting device is deformed to a shape different from the memory shape, specifically to a shape like a circular arc conforming with the curvature of the nail 2 by deforming the device to be affixed to the nail 2.

In this manner, the correcting device 21 is used to correct the ingrown portion 2a of the nail 2 by fixing the device 21 to the surface of the nail 2. The correcting device 21 is shape-memory-treated by which the device 21 is provided with a shape memory, that is, a flat shape to which the shape of the device 21 is restored. The correcting device 21 shape-memory-treated in this manner is bent and deformed at a temperature lower than the temperature of the human body and higher than the transforming temperature and is then installed onto the nail 2.

In this condition, the shape of the correcting device 21 having the superelastic effect tends to be restored to the original shape, specifically to a flat shape. For this, as shown in FIG. 9B, the device 21 produces elastic force (restoring force) which acts on the nail 2. The elastic force becomes a correcting force for lifting the ingrown portion 2a of the nail 2 to correct the involution of the ingrown portion 2a.

As above-mentioned, the superelastic metals can be deformed over wide range by receiving external force and after removing the external force, in the course of restoration to the original shape, change in force is small and the metals are gradually deformed corresponding to the recovery curve in the figure.

Therefore, the correcting device 21 having the superelastic effect produces correcting force which gradually and continuously acts on the ingrown portion 2a of the nail 2, by which the ingrown portion 2a of the nail 2 is easily and gradually lifted outwardly so that the ingrown portion 2a is corrected without pain.

Especially, because the correcting device 21 having the superelastic effect acts on the nail 2 so as to restore the shape thereof to the original shape, thereby effecting correcting force on the nail 2, no special measure, for example, heating, is required to restore the deformed shape to the original shape.

The correcting device 21 formed from the superelastic material continuously and gradually supply stable corrective force on the nail 2 by the combination of widespread elastic-deformation due to the superelasticity and the restoring force due to appropriate elastic modulus. Therefore, the correcting device 21 is reliable, stably exhibiting excellent corrective characteristics.

In the above-mentioned embodiment, the correcting device 21 is shape-memory-treated to restore to the flat shape. However, the memory shape is not limited to this shape. For example, a shape of curvature can be selected in the memory-process. In this case, the correcting device 21 can be manufactured in an advantageous manner.

Specifically, in order to memory-process to memorize the shape of a curvature, a lengthy tape made from a superelastic alloy is wound around, for example, rod of a diameter of 50 mm and it is laminated. The tape is shape-memory-treated to set up as a restoring temperature at a temperature lower than the temperature of the human body, for example, 30° C. By this, the tape is entirely shape-memory-treated so that the tape has a memory of the shape of curvature. Every time when the wound tape is used, the tape is cut into a required size along the length of the affected part. This allows the device to be used of an appropriate size in an efficient manner.

In the above examples, the correcting device is composed of a tape. This structure is greatly advantageous for manufacturing and handling. In addition, the surface of the correcting device may be coated with a resin such as urethane resin and silicon resin. By this measure, the correcting device damages footwear such as soxes only with difficulties. Also, adhesive force can be readily controlled.

In the above examples, as the superelastic alloy, the Ni/Ti alloy is selected to form the device. Other than the Ni/Ti alloy, copper/zinc ((Cu)/(Zn)) ternary alloys, Copper/aluminum/nickel (Cu/Al/Ni) alloys may be used. These alloys can exhibit sufficient superelasticity.

FIGS. 10A and 10B show an alternative embodiment corresponding to the first embodiment of the present invention. In FIGS. 10A and 10B, the parts corresponding to FIGS. 9A and 9B are represented by the same reference numerals as the FIGS. 9A and 9B.

A correcting device 31 for correcting an ingrown nail, which is composed of a tape is supported by a support member 32 laminated on the device 31. The support member 32 and the device 31 is pressed by a pressing member 33. Support member 32 is affixed to the surface of a nail 2. The present invention includes such embodiment.

The first embodiment of the present invention is not limited to the above-mentioned examples and may be variously modified and practiced.

For example, the materials having the superelastic effect are not limited to metals and alloys and other materials may be used. Also, the shape of the device for correcting an ingrown nail is not limited to the above embodiments. For example, as the device for correcting an ingrown nail, one or a plurality of cylindrical or rectangular filaments shown in FIGS. 11A, 11B may be used. FIG. 11A shows a device 41 for correcting an ingrown nail, which is composed of cylindrical filament. As shown in FIG. 11B, a plurality of filaments is adhered to a nail 2 to form the device 14 for correcting an ingrown nail. The device for correcting an ingrown nail, which is composed of seven cylindrical filaments each of a diameter of 0.3 mm has an excellent effect similarly to that of the above embodiments.

As measures for fixing, to the nail, the device for correcting an ingrown nail using adhesives, either a method for applying the adhesives to the device or a method for applying the adhesives to the nail may be used. Also, the measure for combining the correcting device with the nail is not limited to those using adhesives. For example, a double adhesive tape may be used to fix the correcting device to the nail.

As is clear from the above illustrations, the device for correcting an ingrown nail according to the first embodiment of the present invention produces stable elastic force due to restoring force so as to restore to the original shape (memory shape). The elastic force gradually and continuously acts on the nail as the corrective force. Therefore, the stable corrective force acts continuously on the nail by the combination of widespread elastic-deformation due to the superelasticity and the restoring force due to appropriate elastic modulus without using a large thickness. The correcting device is reliable, stably exhibiting excellent corrective characteristics.

Also, in the case where the Ni/Ti alloy is used as the superelastic material to manufacture the device for correcting an ingrown nail, the device for correcting an ingrown nail, which sufficiently exhibit the superelasticity, can be manufactured. Further, by using one or more cylindrical or rectangular filaments or tape as the superelatic material, the device having the superelastic effect can be manufactured.

Next, a device for correcting an ingrown nail corresponding to a second embodiment of the present invention will be explained.

The device for correcting an ingrown nail according to the second embodiment of the present invention comprises, a support member to be affixed to the nail, and a correcting member supported by the support member and effecting force on the nail in the correcting direction for the ingrown portion of the nail.

The device for correcting an ingrown nail (hereinafter simply called "correcting device" in this embodiment) is characterized in that the surface area of the support member is larger than that of the correcting device and the correcting device is placed and fixed on the surface of the support member.

By this structure, the entire support member covering the surface of the nail 2 receives the elastic force of the correcting device so that the elastic force per unit area of the support member is small. Specifically, the elastic force of the correcting device composed of a filament is distributed on the support member into small elastic force per unit area of the support member. So, the support member effect small elastic force per unit area on the nail. Accordingly, an ingrown portion of the nail receives small elastic force to be bent in the correcting direction so that the nail can be corrected by small force without forcible load.

Also, with such structure, the correcting device is composed of the a filament so that the conditions such as a number, size, and position can be optionally selected and such device is placed on the support member covering the surface of the nail and fixed on the surface.

Specifically, the conditions of the ingrown portion of the nail are estimated and the correcting device is placed on the support member after the conditions of the correcting device are controlled so as to apply appropriately distributed corrective force on the ingrown portion of the nail. For this, the ingrown portion of the nail is certainly corrected by elastic force having appropriate distribution without difficulties.

Further, with such structure, the conditions of the correcting device composed of a filament, such as a number, size, position, and the like are easily controlled. The correcting device so much controlled is then placed on the support member which covers the surface of the nail.

The correcting device may have a structure wherein the correcting device is embedded into the support member having larger area than that of the correcting member.

This structure facilitates correction of the nail with out forcible load on the nail. Also, because the correcting device is embedded into the support member, thereby protecting the correcting device, the correcting device is neither dismounted nor damaged by external force. Thus, the correcting device is reliable and the handling of the device is easy.

In addition, the entire correcting device may be made from superelastic alloys or shape memory alloys.

With this structure, the correcting device can be made from materials which improve the functions of the correcting device.

As is clear from the above illustrations, the device for correcting an ingrown nail corresponding to the second embodiment of the present invention comprises the correcting device capable of producing elastic force which acts on the ingrown portion of the nail as correcting force so that the ingrown portion is oriented in the correcting direction. The correcting device is placed and fixed onto the support member and then the support member is affixed to the nail.

Another method for installing the device for correcting an ingrown nail, comprises affixing the support member on the nail of human toe having the ingrown portion, and then placing and fixing, on the surface of a support member, a correcting device effecting force on an ingrown portion of the ingrown nail of the human toe in the correcting direction for the ingrown portion of the ingrown nail. Also, in another method for installing the device for correcting an ingrown nail comprises, embedding, inside a support member, a correcting device effecting force on an ingrown portion of the ingrown nail of the human toe in the correcting direction for the ingrown portion of the ingrown nail and placing the support member on the nail.

By the above-mentioned method for installing the device for correcting an ingrown nail, device can be installed with ease without large load onto the nail so that the correction of the nail can be performed.

Next, various embodiments of a device for correcting an ingrown nail according to the second embodiment will be explained with reference to the drawings.

FIGS. 12A to 12C show a device for correcting an ingrown nail. In these figures, the reference numeral 51 represents a support member made from a silicon resin, polyurethane resin, or the like. This support member 51 is consisting of a plate having the entire surface of the nail 2 of the hallux 1. Also, the support member 51 forms a curvature conforming with a curved surface of the nail 2 along both the direction along the width directing of the nail (lateral direction) and the direction crossing to the lateral direction (longitudinal direction). The support member 51 has a thickness enough to act on the nail 2 corresponding to elastic force from a correcting member 52 described below. The support member can be formed, for example, by patterning in accordance with the nail 2.

The reference numeral 52 denotes a correcting member placed on the surface of the support member 51. In this embodiment, the correcting member 52 is composed of a filament. Specifically, the correcting member 52 has a smaller area compared to that of the support member 51 whereas the support member 51 has a larger area compared to that of the correcting member 52.

The correcting member 52 formed of a filament, as mentioned below, forms a curvature conforming with a curved surface of the nail 2 along the lateral direction. The correcting member 52 bent to have a shape of curvature tends to restore itself to the original condition and thereby to produce elastic force as restoring force. This restoring force acts on the nail 2 via the support member to restore the ingrown portion of the nail 2 to a planar shape.

Given as materials used for forming the correcting member 52 are metals such as iron type alloys, copper type alloys, titanium type alloys, and the like. Also, synthetic resins such as engineering plastics, fiber reinforced plastics, plastic laminated materials, rubbers, and the like can be used. When these metals or synthetic are resins used for the correcting member, these form a curvature along to the shape of the nail 2 in a elastic area to supply restoring force as the corrective force to the nail 2.

Also, it is desirable that the superelastic materials utilized in the device for correcting an ingrown nail be used as materials for forming the correcting member 52.

It is required for the correcting member 52 composed of a filament to act on the nail 2 by supplying appropriately distributed force for correcting the ingrown portion of the nail 2. For the correcting member 52 composed of a filament, the conditions such as a number, position, interval, size, or the like are set up based on the above conditions to be required and then the correcting member 52 is placed on the support member 51. For example, in FIGS. 12A to 12C, two correcting member 52 with a size almost corresponding to the width of the nail 2 are positioned at a certain interval along the width of the nail 2.

Then, the two correcting member 52 positioned on the support member 51 are each supported and fixed using a holder 53. Using, for example, an adhesive tape as the holder 53, the correcting member 52 is fixed on the support member 51. As shown in FIGS. 12A to 12C, the correcting member 52 is sandwiched between the support member 51 and the adhesive tape 53 adhering to the support member 51.

Here, the correcting member 52 made from metals such as iron type alloys, copper type alloys, titanium type alloys, or the like or synthetic resins such as engineering plastics, fiber reinforced plastics, plastic laminated materials, rubbers, or the like has a flat or filamentary shape, or a shape conforming with the curvature of a normal nail along the width of direction the nail 2. In FIGS. 12A to 12C, the correcting member 52 is pressed by the holder 53 so that its shape is deformed into a curvature conforming the curvature of the nail along the width of the nail 2.

The correcting member 52 made from an alloy having the superelestic effect is shape-memory-treated to acquire a memory of the shape such as flat or filamentary or a shape almost conforming with the curvature of a normal nail. Then the correcting member 52 is supported and fixed onto the support member 51. Here, the shape of the correcting member 52 is deformed into a shape conforming with the curvature of the nail 2 (curvature along the width of the nail 2). Thus, the correcting member 52 supported and fixed onto the support member 51 is deformed along the curvature of the support member 51 thereby to tend to restore to its original condition, thereby generating restoring force which acts on the nail 2.

The device for correcting an ingrown nail, which is produced in the above manner is installed onto the nail 2 by fixing the support member 51 to the surface of the nail 2 using, for example, an adhesive agent 54. As the adhesive agent 54, those having no adverse influence on the nail 2 and the human body are used. The correcting member 52 of the correcting device thus installed onto the nail 2 tends to restore to its original condition and thereby to generate restoring force which acts on the nail 2 via the support member 51. Specifically, the restoring force generated by the correcting member 52 acts on the ingrown portion 2a of the nail 2 as the correction force.

The device for correcting an ingrown nail is easily installed onto the surface of the nail 2 without large load on the nail 2.

Here, the correcting member 52 which is made from metals such as iron type alloys, copper type alloys, titanium type alloys, or the like or synthetic resins such as engineering plastics, fiber reinforced plastics, plastic laminated materials, rubbers, or the like acts on the nail 2 within its maximal elasticity. On the other hand, the correcting member 52 made from a superelastic alloy utilizes restoring force generated at a temperature higher than the transforming temperature.

The nail 2 receives this force from the correcting member 52 via support member 51 so that the ingrown portion 2a of the nail 2 is corrected so as to be flattened or to have the shape of curvature of a normal nail.

As above-mentioned, by the device for correcting an ingrown nail according to the second embodiment of the present invention, the correcting device can be readily installed onto the nail compared with a case where conventional correcting devices are directly installed onto the nail.

Then, in the structure in which the surface area of the support member 51 is larger than that of the correcting member 52, elastic force per unit area of the support member 51 is small because the elastic force from the correcting member is received by the entire surface of the support member 51 covering the surface of the nail 2. Specifically, the elastic force of the correcting member 52 composed of a filament is distributed so that elastic force per unit area of the support member 51 is small. The support member 51 supply small force per unit area on the nail 2. For this, the ingrown portion of the nail 2 receives small force to be bent in the correcting direction and thereby to be easily corrected without too much burden.

Also, in the structure in which the surface area of the support member 51 is larger than that of the correcting member 52, the conditions such as a number, size, position, and the like of the correcting member 52 can be optionally set up and the correcting member 52 is placed on the support member 51 covering the surface of the nail 2. Specifically, the conditions of the ingrown portion 2a of the nail 2 are estimated and the correcting member 52 is placed on the support member 51 after the conditions of the correcting member 52 are controlled so as to supply appropriately distributed corrective force on the ingrown portion 2a of the nail 2. For this, the ingrown portion 2a of the nail 2 is certainly corrected by elastic force having appropriate distribution without difficulties. Especially, the conditions of the correcting member 52 composed of a filament, such as a number, size, position, and the like are easily controlled.

Next, various alternative embodiments according to the second embodiment will be explained.

Figure 14A:
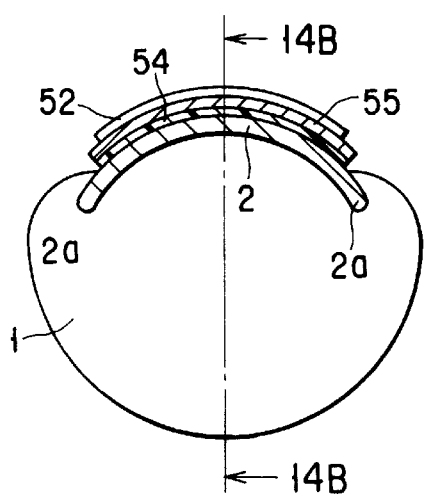
FIGS. 14A and 14B are views of an alternative embodiment of a device for correcting an ingrown nail corresponding to the second embodiment.
Figure 14B:
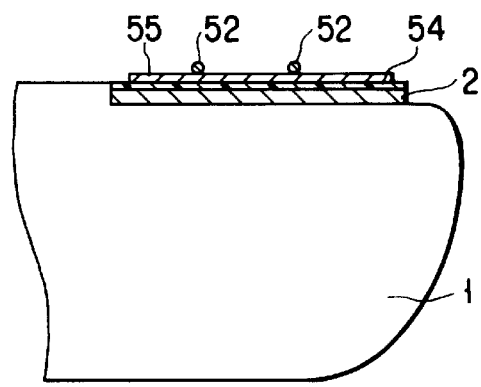

In an embodiment shown in FIGS. 14A and 14B, a support member 55 made from a foaming resin such as a sponge. As shown in FIGS. 14A and 14B, the support member 55 is placed on the surface of the nail 2 and the support member 55 with a cucumber like shape is fixed on the surface of the nail 2 using an adhesive agent. Then, the correcting member 52 composed of a specific number of filaments is on the fixed position of the support member 55 and the correcting member 52 is supported and fixed using the supporter 53 as shown in FIGS. 15A, 15B.

The support member 55 is fixed and bent in the width direction of the nail 2 so that its has a shape of curvature and the correcting member 52 is also bent in the width direction of the nail 2 so that it has a shape of curvature. For this, the correcting member 52 tends to restore to the original condition and thereby to generate restoring force which acts on the nail 2 via the support member 55. The nail 2 receives the restoring force via the support member 51 so that the ingrown portion 2a of the nail 2 is flattened or reformed corresponding to the curvature of a normal nail.

In an embodiment shown in FIG. 16A to 18A, the device for correcting an ingrown nail is assembled, for example, by the following method. As shown in FIGS. 16A, 16B, a supporting raw material 56A formed of a synthetic resin plate is prepared. Multi-channels 56 a are formed on one side of the surfaces of the plate. This supporting raw material 56A is cut into a material with a shape of nail to form a support member 56. The channels 56a is formed in the width direction of the nail 2.

Figure 17A:
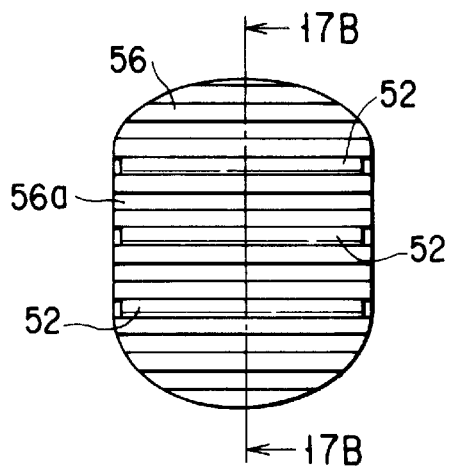
FIGS. 17A and 17B are views of an alternative embodiment of a device for correcting an ingrown nail corresponding to the second embodiment.
Figure 17B:
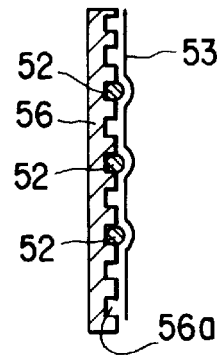
Figure 18:
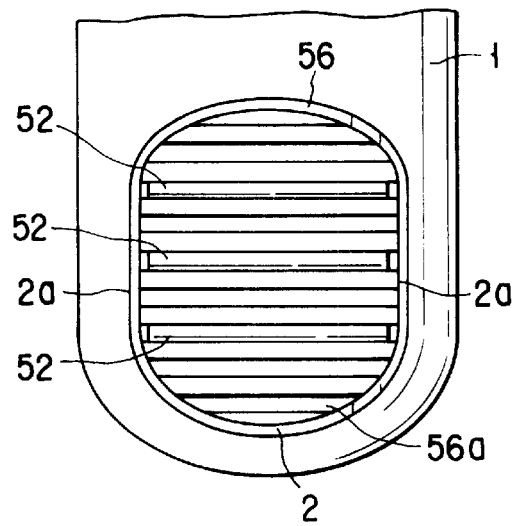
FIG. 18 is a view of an alternative embodiment of a device for correcting an ingrown nail corresponding to the second embodiment.

Next, as shown in FIGS. 17A, 17B, a specific number of the correcting member 52 made of a filament is placed inserted into prescribed numbers of channels among the channels 56a of the support member 56. The correcting member 52 is then supported and fixed using the holder 53. As shown in FIG. 18, the support member 56 is fixed onto the surface of the nail 2 using the adhesive agent 54. Here, the support member 56 is bent in the width direction across the axis of the nail 2 to be fixed. The correcting member 52 is also bent in the width direction of the nail 2. For this, the correcting member 52 tends to restore to the original condition and thereby to generates restoring force which acts on the nail 2 via the support member 56. The nail 2 receives the restoring force via the support member 52 so that the ingrown portion 2a of the nail 2 is flattened or reformed corresponding to the curvature of a normal nail.

The device for correcting an ingrown nail of in this embodiment can be assembled by the following method. Specifically, the support member 56 which is cut into a shape of nail is fixed onto the surface of the nail 2 using an adhesive agent and the correcting member 52 is inserted into the channels 56a of the support member 56, after which the correcting member 52 is supported and fixed by the holder 53.

These affixing treatment can be easily performed without excess load. Therefore, correction of the nail can be easily carried out.

Figure 19A:
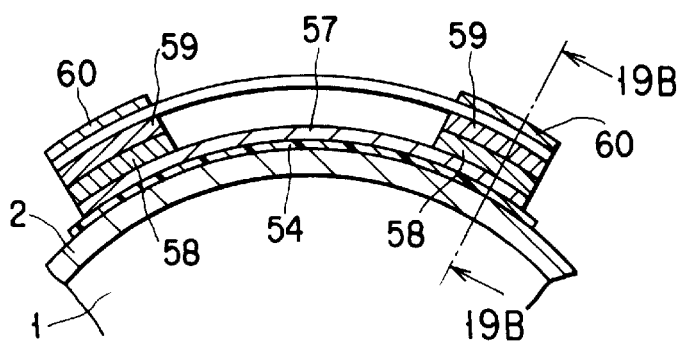
FIGS. 19A and 19B are views of an alternative embodiment of a device for correcting an ingrown nail corresponding to the second embodiment.
Figure 19B:
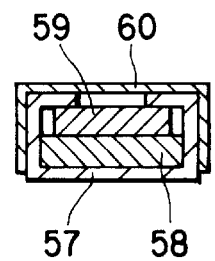

FIGS. 19A, 19B show an embodiment in which a correcting member 58 is made from a superelastic alloy. A support member 57 of a barrel shape, which is made from a synthetic resin is fixed on the surface of the nail 2 using the adhesive agent 54. The correcting member 58 made from a superelastic alloy and a metal chip 59 are placed and fixed, using an adhesive tape 60, onto a part of the support member 57, for example, both ends of the support member 57. The affixing treatment for the device for correcting an ingrown nail can be easily performed without excess load. Therefore, correction of the nail can be easily carried out.

Next, an embodiment shown in FIGS. 20A to 22 will be explained.

In FIGS. 20A to 21, a support member 61 of a plate made from a synthetic resin such as a silicone resin, polyurethane resin, or the like has a shape of nail. A plurality of holes 61a extending in the width direction of the nail 2 is formed inside the support member 61 in order. This support member 61 is, as shown in FIGS. 20A, 20B, formed by cutting a supporting raw material 21A into a shape of nail.

As shown in FIG. 21, a correcting member 62 of a filament is inserted into a part or all of the holes of the support member 61. As the material used for the correcting member 52, metals such as iron type alloys, copper type alloys, titanium type alloys, or the like or synthetic resins such as engineering plastics, fiber reinforced plastics, plastic laminated materials, rubbers, or the like can be used. These metals or synthetic resins are bent conforming with the shape of the nail 2 within their elasticity and supply corrective force to the nail 2 due to restoring force.

Also, shape memory metals and superelastic metals such as copper/zinc ternary alloys, copper/aluminum/nickel alloys, and nickel/titanium alloys can be used as the material for the correcting member 62. A specific number of the correcting member 62 is inserted into prescribed holes 61a corresponding to the conditions of the ingrown portion 2a of the nail 2 so as to act on the nail 2 as an appropriate corrective force. Specifically, the correcting member 62 is embedded inside the support member 61. The diameter of each the holes 61a is made larger than the outside diameter of the correcting member 62.

Figure 22:
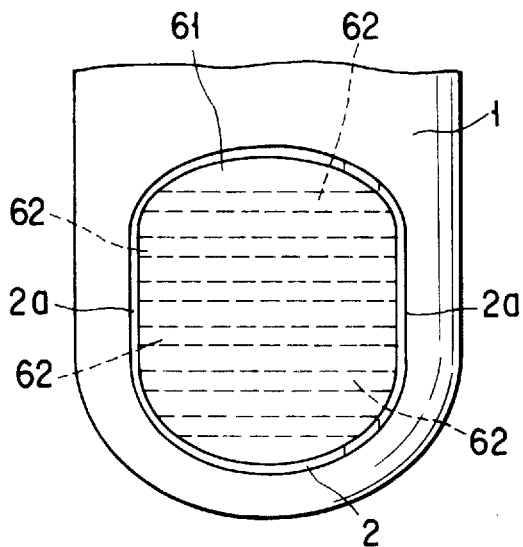
FIG. 22 is a view of an alternative embodiment of a device for correcting an ingrown nail corresponding to the second embodiment.

As shown in FIG. 22, the support member 61 is fixed onto the surface of the nail 2 using the adhesive agent. The support member 61 is bent along the direction across the axis of the nail 2 to be fixed. The correcting member 62 is also bent along the width direction of the nail 2. For this, the correcting member 62 tends to restore to the original condition and thereby to generates restoring force which acts on the nail 2 via the support member 61. The nail 2 receives the restoring force via the support member 61 so that the ingrown portion 2a of the nail 2 is flattened or reformed corresponding to the curvature of a normal nail.

In addition, after the support member 61 is fixed onto the nail 2, the correcting member 62 can be inserted.

By the device for correcting an ingrown nail comprising placing the correcting member 52 inside the support member 61, the ingrown nail can be corrected without forcible burden on the nail 2. Especially, the correcting member 62 is neither dismounted from the support member 61 nor damaged, exhibiting high reliability and easy handling capability.

Here, an example of materials and dimensions used for the correcting member 62 and the support member 61 will be explained. Wire of superelastic Ni/Ti alloy: 0.4 mm diameter, three pieces; strip of superelastic Ni/Ti alloy: 0.2 mm thickness, 2 to 3 mm width; strip of Ni/Ti shape memory alloy: 0.2 mm thickness, 2 to 3 mm width; wire of stainless steel: 0.4 mm diameter, one piece; strip of stainless steel: 0.1 mm thickness, 3 mm width; wire of Co/Cr alloy: 0.4 mm diameter, one piece; strip of Co/Cr alloy: 0.1 to 0.15 mm thickness, 3 mm width; wire of G-FRP: 0.4 mm diameter, ten pieces; dimension of support member: 5 to 10 mm×15 mm width.

Figure 24:
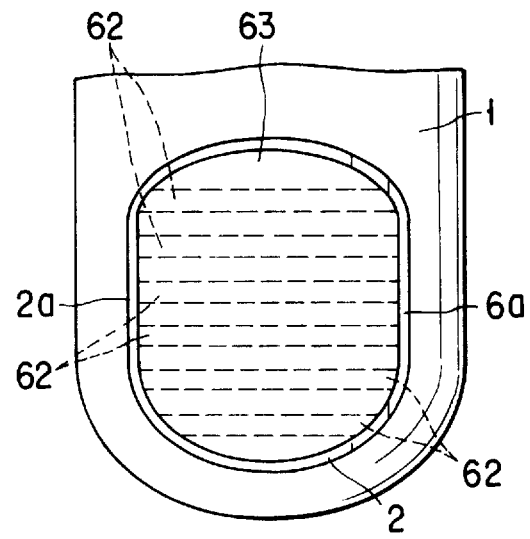
FIG. 24 is a view of an alternative embodiment of a device for correcting an ingrown nail corresponding to the second embodiment.
Figure 23A:
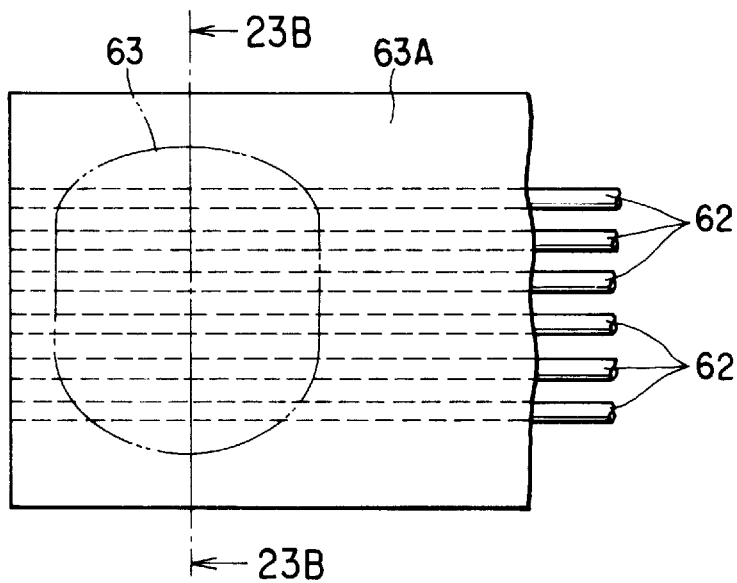
FIGS. 23A and 23B are views of the material for the device for correcting an ingrown nail corresponding to the second embodiment.
Figure 23B:
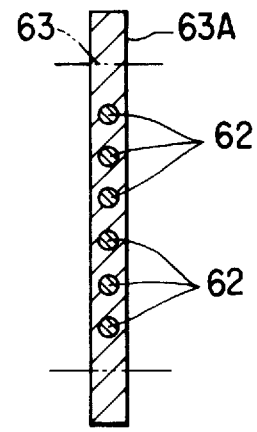

In an embodiment shown in FIGS. 23A, 23B, 24, a plurality of correcting member 62 of a filament extending in the width direction of the nail 2 is embedded in line in the width direction of the nail 2 inside the lengthy supporting raw material 6A which is made from a synthetic resin, e.g. silicone rubber, and which is rectangular in section. The supporting raw material 6A is cut to form the support member 63 of a nail shape. Here, the supporting raw material 6A is cut so that each the correcting member 62 is positioned in line in the width direction of the nail 2. In this case, splicing yarns may be wound up around the support member 23A to improve the strength of the raw material.

As shown in FIG. 24, the support member 63 is fixed onto the surface of the nail 2 using the adhesive agent. The support member 63 is bent in the width direction of the nail 2 to be fixed. The correcting member 62 is also bent in the width direction of the nail 2. For this, the correcting member 62 tends to restore to the original condition and thereby to generates restoring force which acts on the nail 2 via the support member 63. The nail 2 receives the restoring force via the support member 63 so that the ingrown portion 2a of the nail 2 is flattened or reformed corresponding to the curvature of a normal nail.

The device for correcting an ingrown nail according to the second embodiment of the present invention is not limited to the above-mentioned embodiments and various modifications may be made and practiced. As the material used for the support member, ceramics can be used other than metals or synthetic resins.

The material used for the correcting member is not limited to metals or alloys and other various materials such as bimetal may be used. Also, the configuration of the device for correcting an ingrown nail is not limited to the above examples. For example, as the material used for the correcting member, a strand material, tape, net material, or the like can be used other than a strip.

Next, with respect to a typical wire used for the correcting member, various relations such as, a relation between displacement and load and with respect to a typical shape memory alloy, a relation between temperature and load, will be explained.

A wire as a major material used for the device for correcting an ingrown nail and other comparative materials were deformed using a method shown in FIG. 25 and forces were measured when loading and unloading. This method includes, placing a wire 73 on two element material 71 with a diameter of 7 mm and pushing the wire 73 with a element material 72. Elastic restoring force is effective for corrective action. The diameter of the wires of each material is 0.4 mm.

Figure 27:
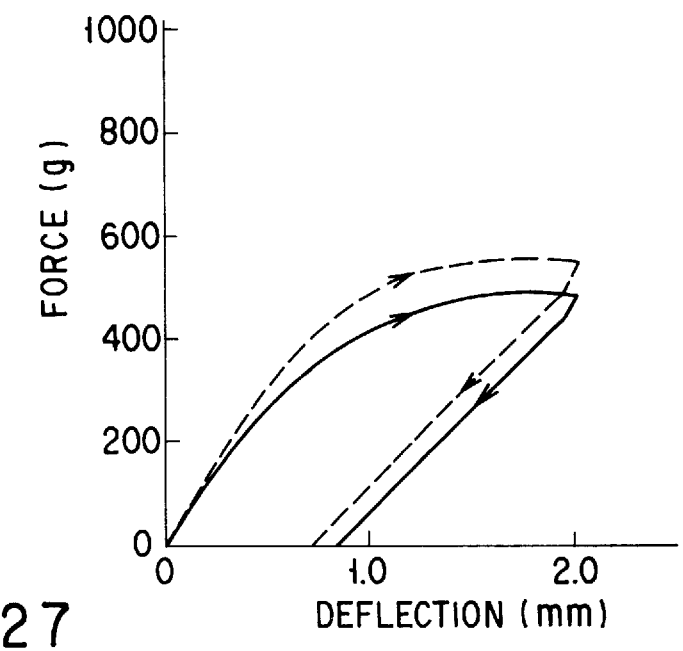
FIG. 27 is a graph showing the relation between load and displacement with respect to wire of cobalt and chromium (Co-Cr) alloy.

FIGS. 26 and 27 each show the relation between load and displacement of stainless steel and a cobalt/chromium (Co/Cr) alloy respectively. The shapes of curves illustrating the relations between the load and the displacement of stainless steel and the Co/Cr alloy are slightly different due to difference in mechanical characteristics. However, when gradually reducing the load after each material bent up to a certain point (2 mm in this experiment), as shown by the arrow, the load is reduced as the displacement is reduced. This load corresponds to the correcting force. The difference between the curves illustrating the load to the displacement of stainless steel (FIG. 26) and the Co/Cr alloy (FIG. 27) is because, as shown by the curve in FIG. 27, the Co/Cr alloy has a low yielding point, the permanent strain of this alloy is larger.

Figure 28:
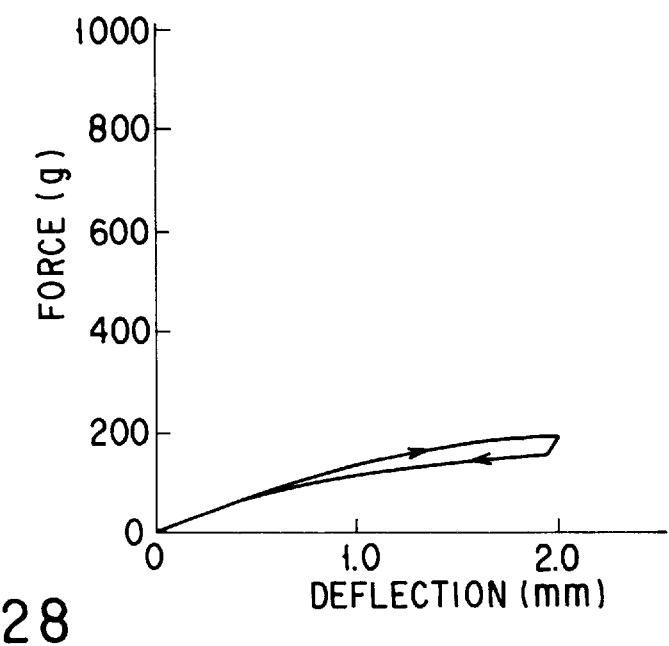
FIG. 28 is a graph showing the relation between load and displacement with respect to wire of super elastic material.

FIG. 28 shows the relation between the load and the displacement for a superelastic material. In this case, as shown in FIG. 28, because the elastic modulus of this material is low (1/4 in this data, generally 1/2.5 to 1/4), the load is lower. However, restoring force is small at the unloading and almost constant load (restoring force) can be obtained in a wide range (of the displacement). The load (storing force) is absolutely low. Therefore, if larger force is required, the number of wires may be increased. For example, with respect to force, two filaments of the stainless correspond to three or four wires of the Ni/Ti alloy.

Figure 29:
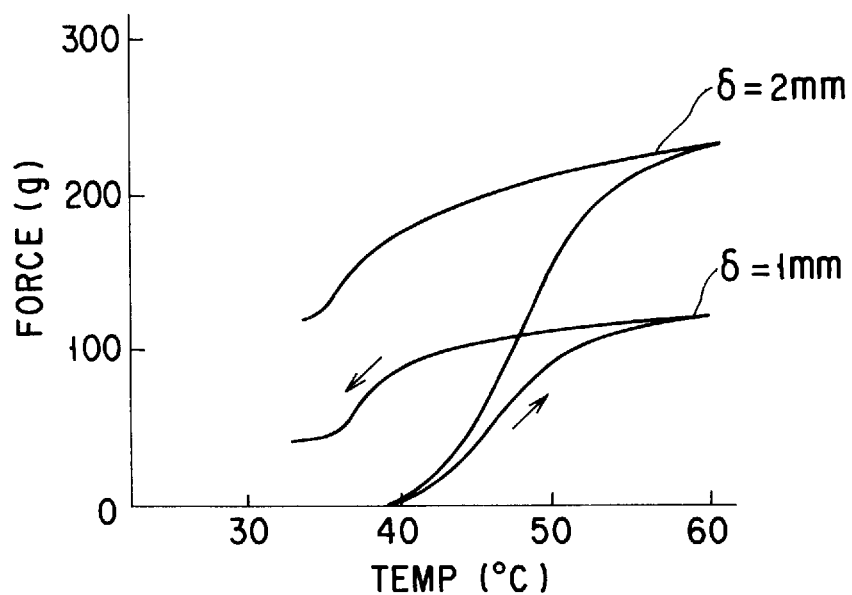
FIG. 29 is a graph showing the relation between load and displacement with respect to wire of shape-memory alloy.

FIG. 29 shows the relation between the load and the displacement with respect to a shape memory alloy. In this case, the shape memory alloy forms a soft layer (cold layer, specifically, martensite layer) at room temperature. Therefore, In the condition when the shape memory alloy is bent with a specific displacement as shown in the FIG. 25, temperature is raised. The force gradually increases around the transformation temperature (As). The position (displacement) at which the maximal force generates changes from the original position (displacement), as the temperature changes. Therefore, in actual use, heating may be controlled according to the conditions such as a degree of pain and the like.

Figure 30:
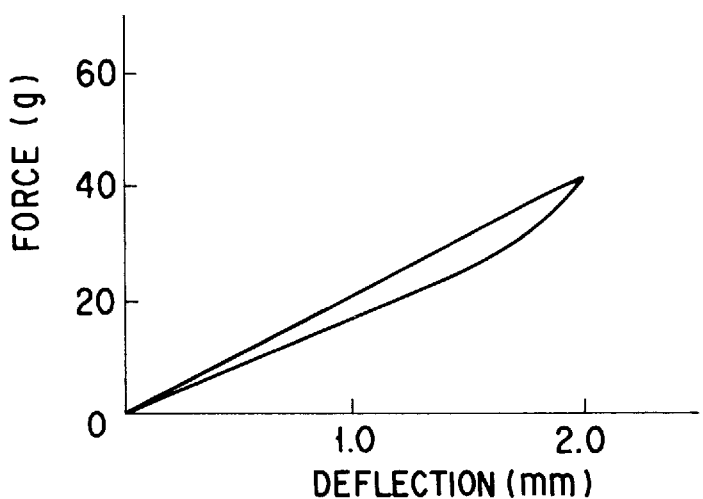
FIG. 30 is a graph showing the relation between load and displacement with respect to GRP.

FIG. 30 shows the relation between the load and the displacement with respect to polyester reinforced by glass fiber. The elastic modulus of this material is small so that the load is small.

Preferable measures for installing the device for correcting an ingrown nail onto the nail comprise a method for applying an adhesive agent to the support member and a method for applying an adhesive agent to the nail. Also, a measure for installing the device for correcting an ingrown nail to the nail is not limited to methods of using an adhesive, and, for example, it is possible to fix the device for correcting an ingrown nail to the nail using a double adhesive tape. Also, the surface of the correcting device may be coated with a resin such as urethane resin and silicon resin. By this measure, the device damages footwear such as soxes only with difficulties. Also, adhesive force can be readily controlled.

As above-mentioned, by the device for correcting an ingrown nail according to the second embodiment of the present invention, the correcting device can be readily installed onto the nail compared with a case where conventional correcting devices are directly installed onto the nail.

Then, in the structure in which the surface area of the support member is larger than that of the correcting member, elastic force per unit area of the support member is small because the elastic force from the correcting member is received by the entire surface of the support member covering the surface of the nail. Specifically, the elastic force of the correcting member composed of a filament is distributed so that elastic force per unit area of the support member is small. The support member supplies small force per unit area on the nail 2. For this, the ingrown portion of the nail 2 receives small force to be bent to the correcting direction and thereby to be easily corrected without too much burden.

Also, in the structure in which the surface area of the support member is larger than that of the correcting member, the conditions such as a number, size, position, and the like of the correcting member can be optionally set up and the correcting member is then placed on the support member covering the surface of the nail. Specifically, the conditions of the ingrown portion of the nail are estimated and the correcting member is placed on the support member after the conditions of the correcting member are controlled so as to apply appropriately distributed corrective force on the ingrown portion of the nail.

Also, in the structure in which the surface area of the support member is larger than that of the correcting member, especially, the conditions of the correcting member composed of a wire, such as a number, size, position, and the like are easily controlled.

In the structure in which the correcting member is embedded inside the support member, the ingrown nail can be corrected without forcible burden on the nail in the similar manner as in the structure according to the first embodiment of the invention. Also, because the correcting member is embedded inside the support member so that the correcting member is protected, the correcting member is neither dismounted from the support member nor damaged, exhibiting high reliability and easy handling characteristics.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalent.

We claim:

1. A device for correcting an ingrown nail, which is adapted to be installed onto a nail of a human toe to correct the ingrown nail, comprising a superelastic tape consisting essentially of nickel/titanium alloy which is shaped-memory-treated to memorize a first shape, and which is deformed to a second shape different from the first shape so as to be installed onto a surface of the nail of the human toe in said second shape.

2. A device for correcting an ingrown nail, which is adapted to be installed onto a nail of a human toe to correct the ingrown nail, comprising a superelastic wire, consisting essentially of nickel/titanium alloy which is shaped-memory-treated to memorize a first shape, and which is deformed to a second shape different from the first shape so as to be installed onto a surface of the nail of the human toe in said second shape.

3. A device for correcting an ingrown nail, which is adapted to be installed onto a nail of a human toe, comprising:

a support member to be installed onto the nail; and a correcting member supported by the support member and effecting force on the nail in a correcting direction of the nail;

wherein said support member has a larger area than that of said correcting member, and said correcting member consisting essentially of nickel/titanium alloy which is placed and fixed onto said support member, and which is formed of one of a superelastic tape and a superelastic wire.

4. A device for correcting an ingrown nail, which is adapted to be installed onto a nail of a human toe, comprising:

a support member to be installed onto the nail; and a correcting member supported by the support member and effecting force on the nail in a correcting direction of the nail;

wherein said support member has a larger area than that of said correcting member, and said correcting member consisting essentially of nickel/titanium alloy which is embedded inside said support member, and which is formed of one of a superelastic tape and a superelastic wire.

* * * * *